United States Patent
Holland et al.

(10) Patent No.: US 9,675,830 B2
(45) Date of Patent: Jun. 13, 2017

(54) AGILITY LADDER

(71) Applicant: Pro Performance Sports, L.L.C., Carlsbad, CA (US)

(72) Inventors: Allen Keith Holland, Carlsbad, CA (US); Daniel John Wray, Carlsbad, CA (US); Kash Oris Bell, Carlsbad, CA (US)

(73) Assignee: PRO PERFORMANCE SPORTS, L.L.C., Carlsbad, CA (US)

( * ) Notice: Subject to any disclaimer, the term of this patent is extended or adjusted under 35 U.S.C. 154(b) by 0 days.

(21) Appl. No.: 14/459,744

(22) Filed: Aug. 14, 2014

(65) Prior Publication Data

US 2015/0224379 A1    Aug. 13, 2015

Related U.S. Application Data

(60) Provisional application No. 61/939,553, filed on Feb. 13, 2014.

(51) Int. Cl.
*A63B 22/00* (2006.01)
*A63B 5/20* (2006.01)
(Continued)

(52) U.S. Cl.
CPC ............... *A63B 5/20* (2013.01); *A61F 7/10* (2013.01); *A61H 15/00* (2013.01);
(Continued)

(58) Field of Classification Search
CPC ......... A63B 17/00; A63B 17/02; A63B 17/04; A63B 23/0458; A63B 67/00; A63B 69/00;
(Continued)

(56) References Cited

U.S. PATENT DOCUMENTS 33,963 A * 12/1861 Shannon ................... E06C 1/56
182/164
308,179 A * 11/1884 Linnenbrink ............. E06C 1/56
182/164
(Continued)

FOREIGN PATENT DOCUMENTS

JP    2005-282290    10/2005
WO    2013/132989    9/2013

OTHER PUBLICATIONS

SKLZ, Quick Flat Rung Agility Ladder, www.amazon.com (Jan. 1, 2013).
(Continued)

*Primary Examiner* — Loan H Thanh
*Assistant Examiner* — Gregory Winter
(74) *Attorney, Agent, or Firm* — Torrey Pines Law Group, PC; Kevin Buckley

(57) ABSTRACT

An agility ladder has a plurality of rungs including first and second rungs. A left link assembly has ends pivotally attached to left ends of the first and second rungs, and a right link assembly has ends pivotally attached to right ends of the first and second rungs. The left and right link assemblies each include first and second links having equal lengths, with the first and second links joined at a link pivot joint which allows the first and second links to form an angle between them of less than 180 degrees.

19 Claims, 5 Drawing Sheets

(51) Int. Cl.
*A61H 15/00* (2006.01)
*A63B 21/00* (2006.01)
*A63B 69/00* (2006.01)
*A61F 7/10* (2006.01)
*A61F 7/00* (2006.01)

(52) U.S. Cl.
CPC .......... *A63B 21/0004* (2013.01); *A63B 69/00* (2013.01); *A61F 2007/0087* (2013.01); *A61F 2007/108* (2013.01); *A61H 2015/0042* (2013.01); *A61H 2015/0064* (2013.01); *A61H 2201/0153* (2013.01); *A61H 2201/0214* (2013.01); *A61H 2201/0257* (2013.01)

(58) Field of Classification Search
CPC ..... A63B 71/00; A63B 21/0004; A63B 23/04; A63B 23/0464; A63B 29/00; A63B 29/02; A63B 2210/50; A63B 2210/52; A63B 2210/54; A63K 3/00; Y10T 403/32549; Y10T 403/32557; Y10T 403/32591
USPC .......... 182/196–198, 21, 22, 67.4, 156, 164; 473/414, 415, 438, 440; 434/247, 251, 434/255, 258; 273/440, 441, 444
See application file for complete search history.

(56) References Cited

U.S. PATENT DOCUMENTS

| | | | | |
|---|---|---|---|---|
| 320,114 | A * | 6/1885 | Bormann | E06C 1/56 182/164 |
| 628,824 | A * | 7/1899 | Maier | E06C 1/56 182/164 |
| 2,370,728 | A * | 3/1945 | Hopp | E06C 1/56 182/197 |
| 3,757,896 | A * | 9/1973 | Lee | E06C 1/56 182/164 |
| 4,059,268 | A * | 11/1977 | Forrest | A63B 69/0028 473/440 |
| 4,067,413 | A * | 1/1978 | Olsen | E06C 1/56 182/164 |
| 4,078,793 | A * | 3/1978 | Allen | A63C 19/06 473/414 |
| 4,260,039 | A * | 4/1981 | Arato | E06C 1/56 182/155 |
| 5,211,260 | A * | 5/1993 | Toycen | E06C 1/56 182/164 |
| 6,945,360 | B2 * | 9/2005 | Sullivan, Jr. | E04G 1/28 182/151 |
| 6,955,631 | B2 * | 10/2005 | Chen Wu | A63B 23/0464 182/196 |
| 7,874,959 | B2 * | 1/2011 | Dieter | A63B 23/0464 473/414 |
| 8,574,133 | B2 | 11/2013 | Dieter | |
| 2010/0298074 | A1 * | 11/2010 | Esposito | A63B 69/00 473/438 |
| 2011/0114419 | A1 * | 5/2011 | Merey | E06C 1/383 182/152 |
| 2011/0174754 | A1 * | 7/2011 | Entz | A47B 43/00 211/202 |
| 2012/0077644 | A1 | 3/2012 | Dieter | |
| 2015/0045187 | A1 * | 2/2015 | Tani | A63B 23/0458 482/23 |
| 2015/0060204 | A1 * | 3/2015 | Walter | E06C 1/383 182/163 |

OTHER PUBLICATIONS

International Preliminary Report on Patentability issued in PCT/US2015/015265 on Aug. 16, 2016 (8 pages).

* cited by examiner

AGILITY LADDER

PRIORITY CLAIM

This Application claims priority to U.S. Provisional Patent Application No. 61/939,553 filed Feb. 13, 2014, and incorporated herein by reference.

BACKGROUND OF THE INVENTION

Agility ladders are used to improve speed and agility. Generally an agility ladder has lateral rungs attached to left and right side strips of webbing. The rungs are often plastic tubes, rods or strips. When unrolled or laid out on the ground, the agility ladder forms a column of open boxes or spaces. Depending on the specific training exercise the user's objective is to run, jump or hop through the ladder using a predetermined pattern of foot placement. Although these types of agility ladders have advantages, drawbacks with them remain. For example, the webbing can become tangled, causing delays in set up. The rungs in these types of agility ladders are also easily displaced by a user's foot, requiring frequent adjustment during use. Improved designs are needed.

SUMMARY OF THE INVENTION

In one aspect, an agility ladder has a plurality of rungs. A left link assembly has ends pivotally attached to left ends of first and second rungs, and a right link assembly has ends pivotally attached to right ends of the first and second rungs. The left and right link assemblies each include first and second links joined at a link pivot joint which keeps the links in an under center position, so that the links do not become precisely parallel when the ladder is deployed.

BRIEF DESCRIPTION OF THE DRAWINGS

In the drawings the same reference number indicates the same element in each of the views.

DETAILED DESCRIPTION OF THE DRAWINGS

Figure 1:
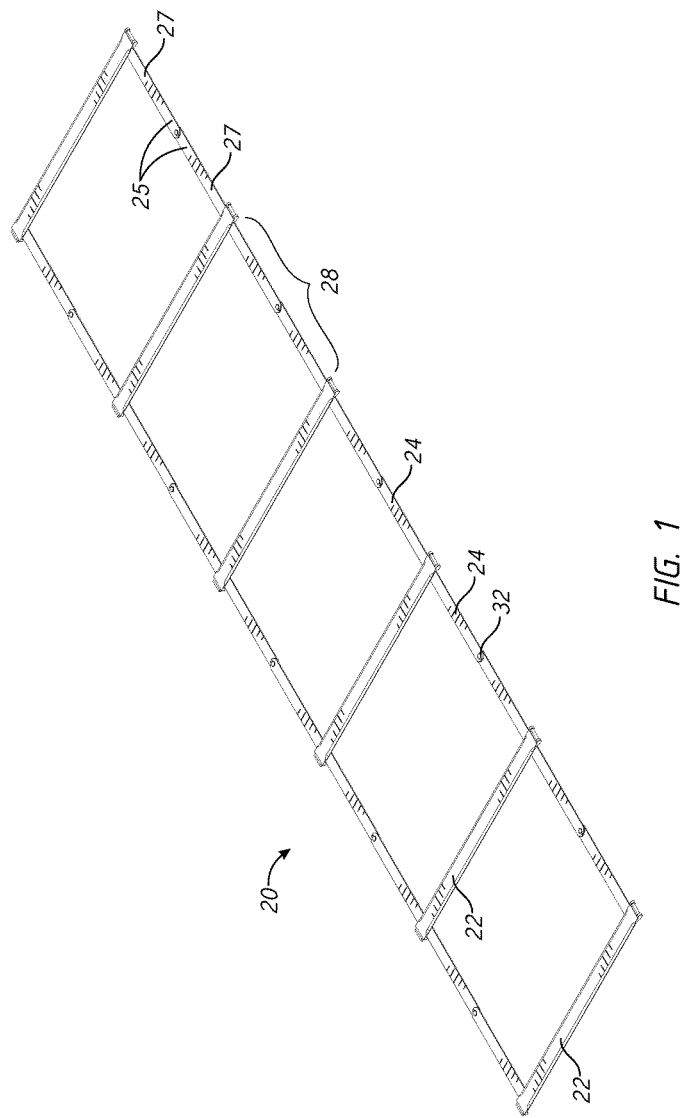
FIG. 1 is a top perspective view of an agility ladder in the deployed position and ready for use.
Figure 2:
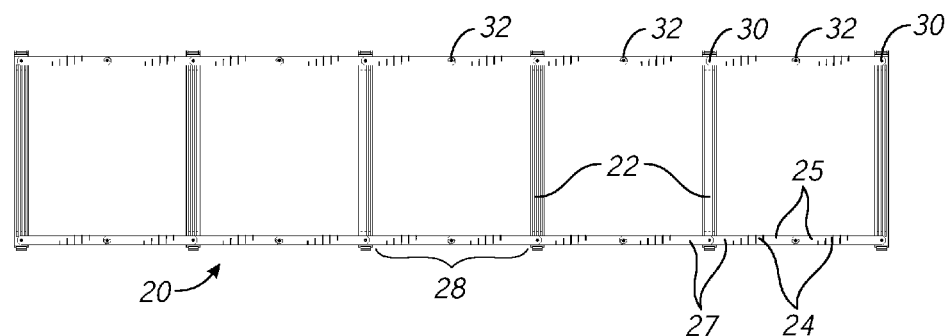
FIG. 2 is a plan view of the agility ladder as shown in FIG. 1.

As shown in FIGS. 1-4, an agility ladder 20 includes lateral rungs 22 pivotally connected via folding longitudinal link assemblies 28. Each link assembly 28 includes two links 24, with the inner ends 25 of the links joined to each other at a link pivot join 32, and with the outer end 27 of each link joined to a rung 22 via a rung pivot joint 30. The rungs 22, which may all be the same, typically are 30-100 cm long and 4 to 10 cm wide.

Figure 7:
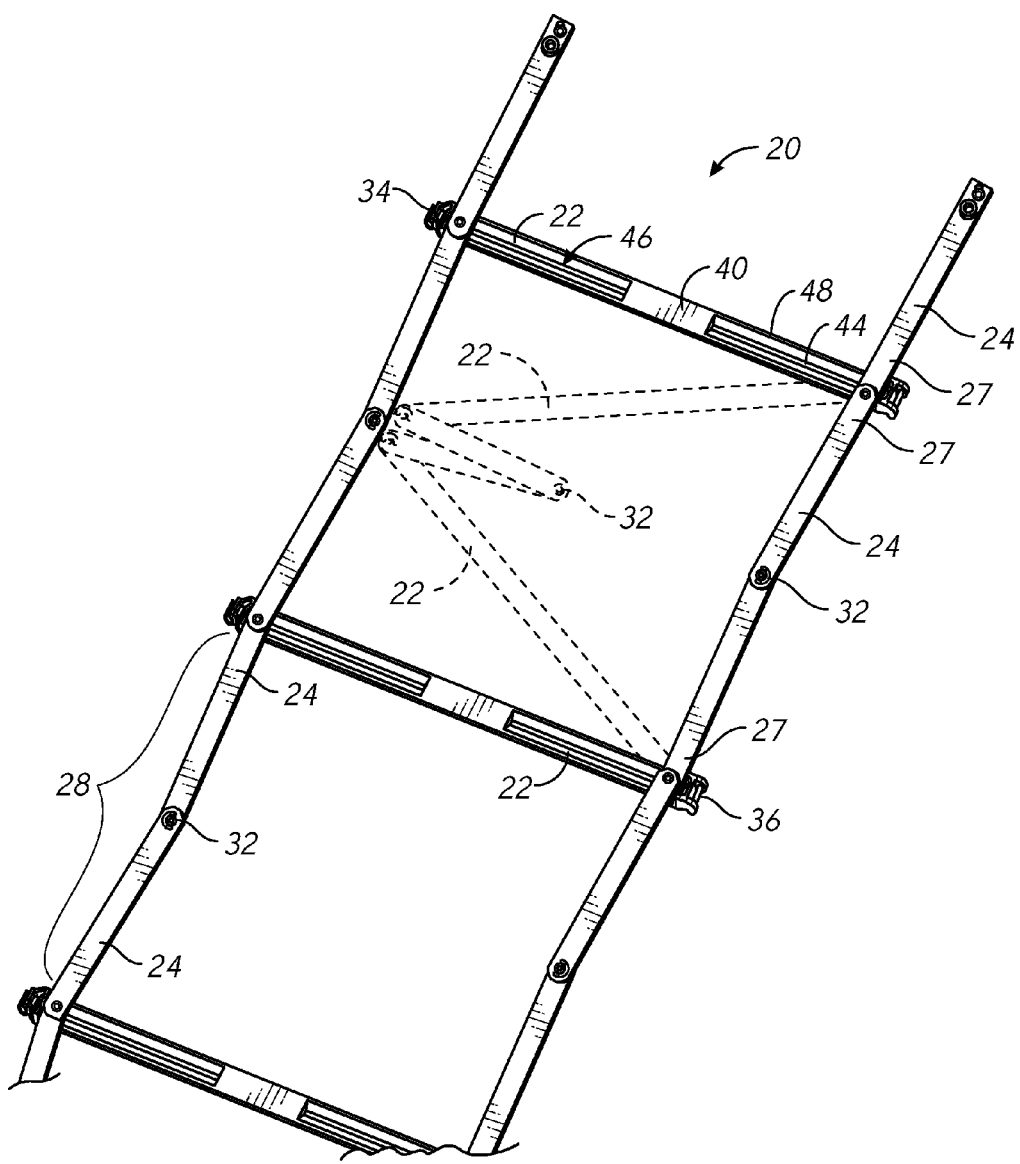
FIG. 7 is an enlarged bottom perspective view of the agility ladder in the deployed position.

The rung 22 may have a flat bottom surface so that the rung lays flat on the ground. Referring to FIG. 7, substantially the entire length of the rung 22 may be continuous and flat, or the rung may have one or more solid flat bottom sections 40 and ribs 44 and recesses 46. These features may be molded into the rung during manufacture if the rung is made of a plastic material. The bottom surface of each rung may lay in a common plane.

Figure 5:
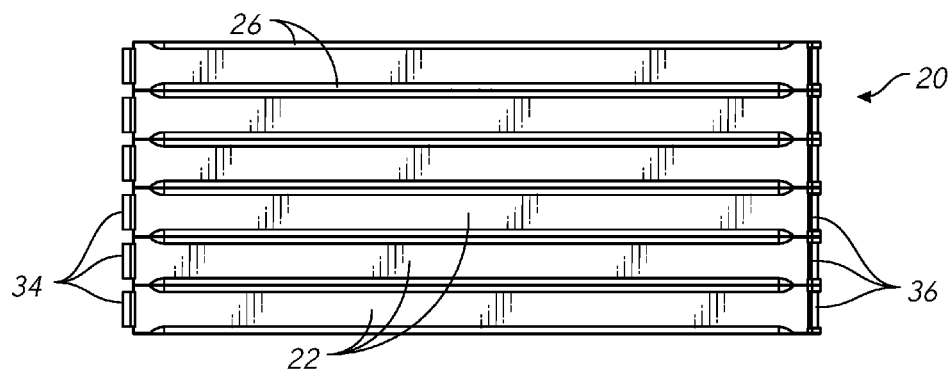
FIG. 5 is a plan view of the agility ladder of FIGS. 1-4 now shown in the folded position.
Figure 8:
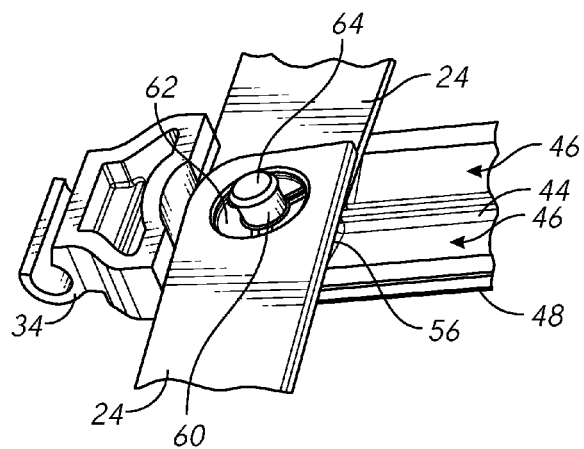
FIG. 8 is an enlarged bottom perspective view of a rung pivot joint.

Turning to FIGS. 7-10, the outer ends 27 of adjacent links 24 are pivotally attached onto the bottom surface of the rung 22 at the left and right ends of the rung via a rung pivot joint 30. The rung pivot joint 30, in the example shown, may have a pivot post 60 on the rung projecting through holes in the outer ends of the links, with a post head 64 retaining the links onto the pivot post 60, optionally with a washer 62 between them. As shown in FIG. 8, where the bottom of the rung 22 has recesses 46, one or more ribs 44 may be provided between the recesses and parallel to the edges 48 of the rung 22. The edges 48 may be rounded or angled to better avoid interfering with the user's feet. FIG. 5 shows a design where the edges 48 are angled. The top surface of the rung may be flat or curved.

Figure 9:
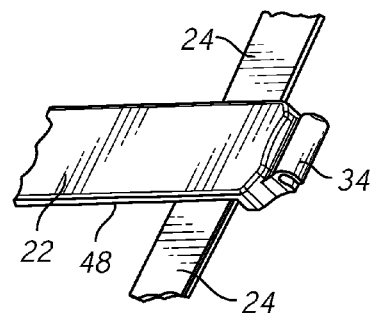
FIG. 9 is a left side perspective view of the agility ladder section shown in FIG. 8.
Figure 10:
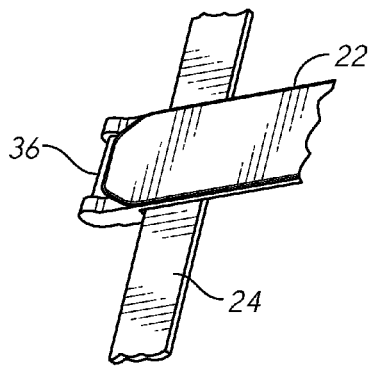
FIG. 10 is a right side perspective view of the agility ladder section shown in FIG. 8.

Referring still to FIG. 8, the left and right ends of the rung 22 may formed as a solid end block 56 to better support the pivot post 60. As shown in FIGS. 7-10, the inner and outer ends of the links 24 may be rounded or chamfered. As illustrated in FIGS. 8-10, a first fitting 34 may be provided on the right end of the rung, and a second complimentary fitting 36 provided on the left end of the rung 22. The fittings are complimentary in that they are designed to engage with or into each other. In the example shown, the fittings are a hook and a bar, respectively. Where two or more agility ladders 20 are used side-by-side to form two or more columns, the fittings allow adjacent ladders 20 to be attached to each other. Of course, various other types of fittings may equivalently be used, such as snaps, pins, interlocking tabs, etc.

Figure 3:
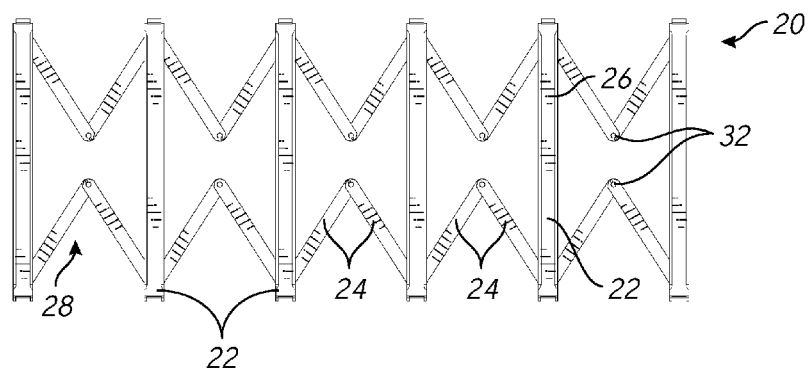
FIG. 3 is a plan view of the agility ladder of FIG. 1 in an intermediate position between the deployed position shown in FIG. 1 and a folded or collapsed position.
Figure 4:
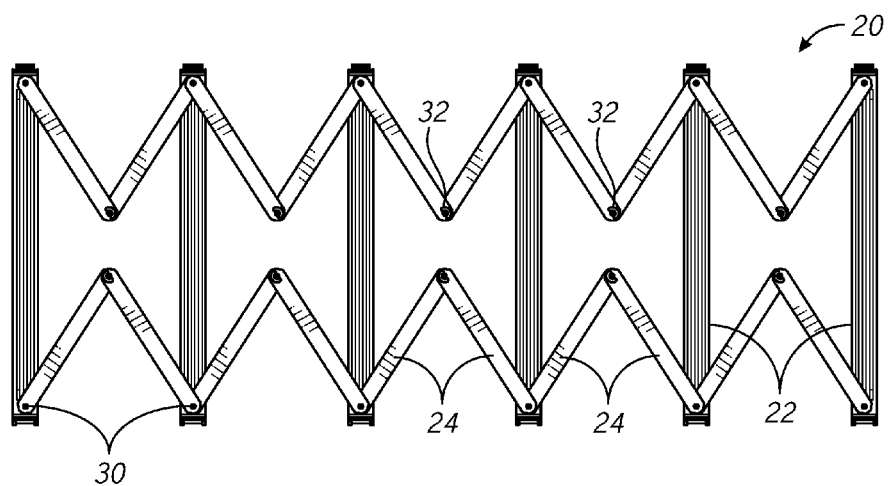
FIG. 4 is a bottom view of the agility ladder as it is shown in FIG. 3.
Figure 11:
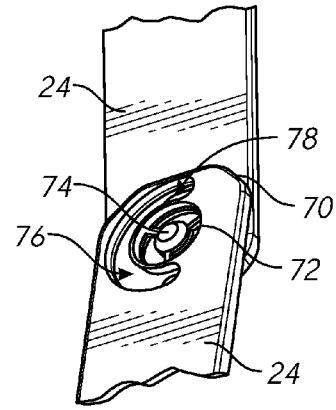
FIG. 11 is a bottom perspective view of a link pivot joint.
Figure 12:
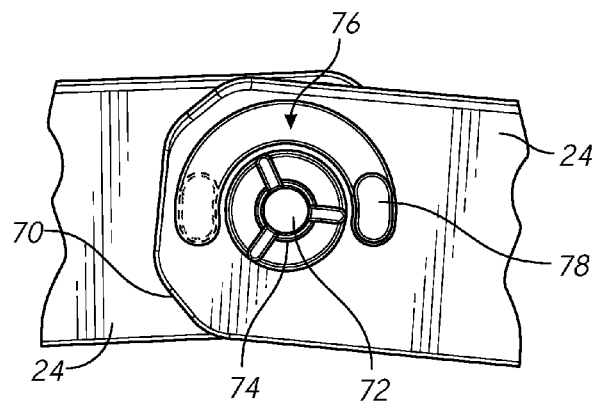
FIG. 12 is a plan view of the link pivot joint shown in FIG. 11.

Turning to FIGS. 11 and 12, the link pivot joint 32 is designed so that the link assembly 28 can only fold inwardly as shown in FIG. 3, and not outwardly. The link pivot joint 32 is also designed to maintain the two links 24 of the link assembly 28 at an angle less than 180 degrees. Generally the angle between the links 24 is limited to about 165-175 degrees, and a maximum of 179 degrees. Consequently, with the agility ladder fully deployed, there is still a slight angle between the links, as shown in exaggerated form in FIG. 7 for purpose of illustration.

At each link pivot joint 32 both links can pivot freely, and at each rung pivot joint 30, each link and the rung can pivot freely. Consequently, pivoting movement of any link or rung does not transmit torque to any other link or rung. All links may have the same length, and may also be the same part. Generally the link length may be 40 or 45 to 48 or 49% of the rung length. Longer links allows for increased range of spacing between rungs. The links and rungs may be a resilient flexible material, such as plastic, with a thickness of 2-5 mm.

In the example shown, the link pivot joint 32 may include a pivot pin 72 on a first or overlying link extending through a hole in the a second or underlying link, with a pin head 74 retaining the second link onto the pivot pin 72, and to form a pivoting connection between the first and second links. To limit the movement of the link pivot joint to 179 degrees or less, a curved lug 78 on the first link may project into an arcuate slot 76 in the second link, with the lug 78 bottoming out at the end of the slot 76 at the limit of travel.

Figure 6:
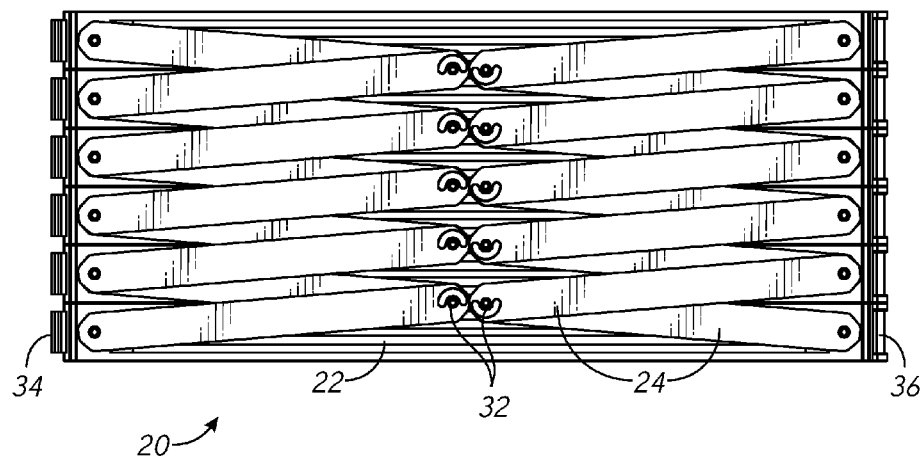
FIG. 6 is a bottom view of the agility ladder as it is shown in FIG. 5.

In use, the agility ladder 20 may be stored or transported in the folded position shown in FIGS. 5 and 6. In this position the rungs may be touching each other, or only minimally spaced apart. The length of the agility ladder 20 when folded is the sum of the combined width of each rung. In most designs, the agility ladder 20 has 4 to 10 rungs, with designs having 5, 6 or 7 rungs most often used. For an agility ladder having 6 rungs as in FIGS. 1-3, and a rung width of 5 cm, the length of the agility ladder 20 in the folded position is 30 cm. The thickness or height of the agility ladder may range from about 6 to 20 mm. The width of the agility ladder is the length of the rungs 22. As a result in the folded position the agility ladder is highly compact. As shown in FIG. 6, in the folded position the inner ends of the links 24 may be minimally spaced apart, e.g., by 1-10 mm.

The agility ladder 20 may be deployed by pulling the end rungs 22 away from each other. Each of the link assemblies acts independently of the other link assemblies. Consequently, the ladder may optionally be deployed on a curve, with the rungs forming acute angles rather than being parallel. In this configuration the ladder may form non-parallelogram shaped spaces. For example, as shown in dotted lines in FIG. 7, a triangle may be formed between adjacent rungs. In addition, any adjacent rungs may be left together with no space formed between them, with non-adjacent rungs forming squares or other shapes. Stakes may optionally be used to secure the ladder onto the ground.

The ladder may optionally be used in a non-fully deployed position as shown in FIG. 3, to provide smaller foot target spaces. The ladder may be refolded by pushing the end rungs towards each other. The link pivot joint 32 insures that the link assemblies 28 remain in an under center configuration so that they fold inwardly when the ladder is folded or collapsed.

Complementary means that the first fitting is designed to engage with the second fitting, to allow two ladders side-by-side to be attached to each other. Substantially parallel means parallel to within 5 degrees or less. Substantially touching each other means actually touching or spaced apart by less than 5 mm.

The rungs attached to each other substantially only by the link assemblies means that there is no other element of consequence in the operation of the ladder attaching them. Inconsequential elements such as a rope, ribbon, or tape that cannot act in both tension and compression, are not excluded.

Thus, a novel agility ladder has been shown and described. Various changes and substitutions may of course be made without departing from the spirit and scope of the invention. The invention, therefore, should not be limited except by the following claims and their equivalents.

The invention claimed is:

1. An agility ladder comprising:
   first and second rungs;
   a left link assembly having ends pivotally attached to left ends of the first and second rungs;
   a right link assembly having ends pivotally attached to right ends of the first and second rungs;
   with the left and right link assemblies each including first and second links having equal lengths, with the first and second links joined at a link pivot joint which limits an angle between the first and second links to 179 degrees or less; and
   a first fitting disposed on the left end of the first rung or the right end of the first rung of the agility ladder, the first fitting structurally configured for cooperation with a second fitting disposed on a second agility ladder to enable attachment and side-by-side use of at least two agility ladders, wherein the second fitting is disposed on an opposite end of a first rung of the second agility ladder from the first fitting.

2. The agility ladder of claim 1 with the first and second rungs attached to each other substantially only by the left and right link assemblies.

3. The agility ladder of claim 1 with the first rung having a length greater than twice the length of the first link.

4. The agility ladder of claim 3 wherein the first and second rungs are substantially the same.

5. The agility ladder of claim 1 with the first link having an arcuate lug extending into an arcuate slot in the second link.

6. The agility ladder of claim 4 wherein the left and right link assemblies pivot inwardly towards each other as the rungs are moved toward each other.

7. The agility ladder of claim 6 with the first link of the left link assembly attached only to the first rung and to the second link of the left link assembly, and with the second link of the left link assembly attached only to the second rung and to the first link of the left link assembly.

8. The agility ladder of claim 7 with the first link of the right link assembly attached only to the first rung and to the second link of the right link assembly, and with the second link of the right link assembly attached only to the second rung and to the first link of the right link assembly.

9. The agility ladder of claim 1 with the rungs moveable from an open position, wherein the rungs are spaced apart, to a collapsed position wherein the rungs are substantially touching each other.

10. The agility ladder of claim 1 with the first fitting disposed at the left end of each rung, and further comprising the second fitting disposed at the right end of each rung, and with the second fitting complementary to the first fitting.

11. An agility ladder comprising:
    first and second rungs each having a length L1;
    a first left link having an outer end pivotally attached to a left end of the first rung;
    a second left link having an outer end pivotally attached to a left end of the second rung, and the second left link having an inner end pivotally attached to an inner end of the first left link at a left link pivot joint;
    a left arcuate lug on the first left link projecting into a left arcuate slot in the second left link;
    a first right link having an outer end pivotally attached to a right end of the first rung;
    a second right link having an outer end pivotally attached to a right end of the second rung, and the second right link having an inner end pivotally attached to an inner end of the first right link at a right link pivot joint;
    a right arcuate lug on the first right link projecting into a right arcuate slot in the second right link;
    with all of the links having a length L2, and with L2 less than one-half of L1; and
    a first fitting disposed on the left end of the first rung or the right end of the first rung of the agility ladder, the first fitting structurally configured for cooperation with a second fitting disposed on a second agility ladder to enable attachment and side-by-side use of at least two agility ladders, wherein the second fitting is disposed on an opposite end of a first rung of the second agility ladder from the first fitting.

12. The agility ladder of claim 11 wherein the left arcuate lug projecting into the left arcuate slot prevents the first left link from moving into a position where the first left link is both parallel to and not overlying the second left link.

13. The agility ladder of claim 1 wherein the first fitting includes a bar and the second fitting includes a hook structurally configured to receive the bar.

14. The agility ladder of claim 1 wherein the first fitting includes one or more of a snap, a pin, or an interlocking tab.

15. The agility ladder of claim 1 wherein each of the first and second rungs includes a substantially flat bottom section disposed between ribbed sections on a bottom surface thereof.

16. The agility ladder of claim 1 wherein one or more of the left link assembly or the right link assembly are capable of being pivoted inwardly to form a triangle with two sides of the triangle formed by the first and second rungs.

17. The agility ladder of claim 1 wherein each of the left link assembly or the right link assembly is capable of being independently pivoted relative to one another.

18. The agility ladder of claim 11 wherein the first fitting includes a bar and the second fitting includes a hook structurally configured to receive the bar.

19. An agility ladder comprising:
   first and second rungs, wherein each of the first and second rungs includes a substantially flat bottom section disposed between ribbed sections on a bottom surface thereof;
   a left link assembly having ends pivotally attached to left ends of the first and second rungs;
   a right link assembly having ends pivotally attached to right ends of the first and second rungs;
   with the left and right link assemblies each including first and second links having equal lengths, with the first and second links joined at a link pivot joint which limits an angle between the first and second links to 179 degrees or less; and
   a fitting disposed on a left side or a right side of the agility ladder, the fitting structurally configured for cooperation with a second fitting disposed on an opposite side of the second agility ladder to enable attachment and side-by-side use of at least two agility ladders.

* * * * *